United States Patent
Okada et al.

(10) Patent No.: US 6,391,652 B2
(45) Date of Patent: May 21, 2002

(54) IMMUNOASSAY METHOD AND IMMUNOASSAY KIT

(75) Inventors: Keisaku Okada; Kenjiro Mori; Shuji Senda, all of Ibaraki (JP)

(73) Assignee: Nitto Denko Corporation, Osaka (JP)

( * ) Notice: Subject to any disclaimer, the term of this patent is extended or adjusted under 35 U.S.C. 154(b) by 0 days.

(21) Appl. No.: 09/120,192

(22) Filed: Jul. 22, 1998

(30) Foreign Application Priority Data

Aug. 7, 1997 (JP) ............................................... 9-213177

(51) Int. Cl.[7] .............................................. G01N 33/53
(52) U.S. Cl. ..................... 436/518; 435/38; 435/7.1; 435/7.94; 435/287.7; 435/287.9; 436/514; 436/21; 436/528; 436/810; 422/56; 422/57; 422/61
(58) Field of Search ......................... 435/38, 7.1, 7.94, 435/287.7, 287.9; 436/21, 514, 518, 528, 810; 422/56, 57, 61

(56) References Cited

U.S. PATENT DOCUMENTS

| | | | |
|---|---|---|---|
| 4,647,654 A | | 3/1987 | Knowles et al. |
| 5,141,850 A | * | 8/1992 | Cole et al. |
| 5,242,804 A | * | 9/1993 | Bahar et al. |
| 5,512,282 A | * | 4/1996 | Krivan et al. |
| 5,965,458 A | * | 10/1999 | Kouvonen et al. |
| 6,080,400 A | * | 6/2000 | Williams et al. |

FOREIGN PATENT DOCUMENTS

| | | |
|---|---|---|
| EP | 0 315 866 A1 | 5/1989 |
| WO | WO 92/02820 | 2/1992 |

* cited by examiner

*Primary Examiner*—Bao-Thuy L. Nguyen
(74) *Attorney, Agent, or Firm*—McGuireWoods LLP

(57) ABSTRACT

An immunoassay method comprising bringing an immobilized phase comprising, at different positions on a water-absorbable base material, at least two first immunity substances capable of specifically binding with at least two kinds of assay target substances selected from the group consisting of verotoxin-producing *Escherichia coli*, verotoxin and human hemoglobin contained in a test sample, into contact with a test sample and a liquid containing labeled immunity substances each comprising a second immunity substance that is labeled with colored particles and capable of binding with said assay target substance, thereby to form an assay target substance-labeled immunity substance complex and to bind said complex with respective first immunity substances at the immobilized phase. The immunoassay method, the immunoassay device and the immunoassay kit of the present invention enable easy and simultaneous analysis of O157 (VTEC), VT and Hb in a test sample, by adsorption of the assay target substances on an immobilized phase and evaluation of the developed color.

7 Claims, 4 Drawing Sheets

IMMUNOASSAY METHOD AND IMMUNOASSAY KIT

TECHNICAL FIELD OF THE INVENTION

The present invention relates to an immunoassay method, an immunoassay device and an immunoassay kit, permitting easy, quick and highly accurate detection of at least two kinds of test substances from verotoxin-producing *Escherichia coli*, verotoxin and human hemoglobin in a test sample simultaneously on the same base material.

BACKGROUND OF THE INVENTION

The O157, which is a verotoxin-producing *Escherichia coli* posing serious problems in recent years, enters the body with foodstuff, which is the main infectious source, and causes the onset of disease after about 4 to 9 days of incubation period. Bloody feces is a symptom seen from the early stages of the infection and, in some cases, hemolytic anemia, renal failure and thrombocytopenia follow due to the action of verotoxin produced by O157. The disease may ultimately progress to cause hemolytic uremic syndrome (HUS).

The operation to detect verotoxin-producing *Escherichia coli* in foodstuff and patients is extremely complicated and requires many days before results are obtained. However, an immunological assay method has recently enabled a comparatively easy detection of the causative source.

A specific detection method includes a method (trademark EHEC-TEC ELISA TEST SYSTEM, manufactured by Organon Teknika Corp.) for detecting O157 antigen, comprising culturing a food using mTSB (Tripticase Soy Broth Modified) medium and applying an ELISA method (enzyme-linked immunosorbent assay method). For the detection of verotoxin production by *Escherichia coli* separated from food, a method (trademark, Verotox-F "SEIKEN", manufactured by Denka Seiken Co., LTD.) includes culture thereof in a CA-YE medium and detection of verotoxin 1 and verotoxin 2 by latex agglutination test using supernatant as a test sample.

A method for detecting O157 in a test sample from a patient includes use of a latex agglutination test (trademark *Escherichia coli* O157detection kit "UNI", manufactured by UNIPATH LTD.).

The above-mentioned methods detect O157 and verotoxin as a single test item, which means that they cannot be detected concurrently. In addition, these methods require enrichment before detection. Thus, they are time-consuming and require complicated manipulation.

On the other hand, an immunity chromatography method has recently been drawing attention as a method permitting quick and easy immunoassay. In this method, the following steps are taken. That is, an immobilized phase on which an immunity substance capable of binding with an assay target substance in a test sample is immobilized on a water absorbable base material, and a label phase comprising a labeled immunity substance capable of binding with said assay target substance, in such a manner that the labeled immunity substance can be released from said base material upon contact with water, are set at specific intervals to give a test strip, and a test sample is absorbed from one end on the label phase side of the strip. Then, the labeled immunity substance is released from the label phase, bound with the assay target substance to form a labeled immunity substance—assay target substance complex, and this complex is bound with an immobilized immunity substance at the aforementioned immobilized phase. By assaying the labeled immunity substance bound at the immobilized phase, the assay target substance in the test sample can be assayed.

The label to be used to give the labeled immunity substance is exemplified by colloidal metallic particle, enzyme, fluorescent material, phosphorescent material, coloring material and water dispersible polymer particles bound with or containing enzyme, fluorescent material, phosphorescent material, coloring material and the like. In particular, a labeled immunity substance wherein water dispersible polymer particles colored with a fluorophosphorescent material, coloring material (e.g., dye and pigment) and the like are bound with an immunity substance by physical adsorption, and a labeled immunity substance obtained by binding gold colloidal particle with an immunity substance are widely used due to high determination sensitivity and easiness.

In the present invention, an immunity chromatography method is used to detect verotoxin-producing *Escherichia coli* which is represented by O157 raising great concerns these days, verotoxin and human hemoglobin associated with intestinal hemorrhage, and an immunoassay method is provided that permits easy, quick, highly accurate and simultaneous detection of these assay target substances.

SUMMARY OF THE INVENTION

According to the present invention, it has been found that, in a conventional immunity chromatography method, the use of a labeled immunity substance wherein a second immunity substance capable of binding with said assay target substances has been labeled with colored particles and an immobilized phase comprising at least two first immunity substances capable of specifically binding with at least two kinds of assay target substances selected from verotoxin-producing *Escherichia coli*, verotoxin and human hemoglobin in a test sample, the first immunity substances being immobilized on different positions on a water-absorbable base material, enables simultaneous detection of plural assay target substances in a test sample.

Thus, the present invention provides the following.

(1) An immunoassay method comprising bringing an immobilized phase comprising, at different positions on a water-absorbable base material, at least two first immunity substances capable of specifically binding with at least two kinds of assay target substances selected from the group consisting of verotoxin-producing *Escherichia coli*, verotoxin and human hemoglobin contained in a test sample, into contact with a test sample and a liquid containing labeled immunity substances each comprising a second immunity substance that is labeled with colored particles and capable of binding with said assay target substance, thereby to form an assay target substance-labeled immunity substance complex and to bind said complex with respective first immunity substances at the immobilized phase.

(2) The immunoassay method of above (1), wherein the contact is made by flowing a mixture of the test sample and the liquid, so that it is absorbed from one end of the water-absorbable base material, thereby to bind said complex with the first immunity substance.

(3) The immunoassay method of above (1), wherein the contact is made by flowing the test sample, so that it is absorbed from one end of the water-absorbable base material, thereby to bind the assay target substance with the first immunity substance, and then flowing the liquid to allow absorption thereof by the base material, thereby to bind said labeled immunity substance with the assay target substance.

(4) The immunoassay method of above (1), wherein the contact is made by having the test sample absorbed halfway up to the immobilized phase, allowing the liquid to be absorbed from one end of the water-absorbable base material, thereby to form a complex of said labeled immunity substance and the assay target substance, and binding said complex with the first immunity substance at the immobilized phase.

(5) The immunoassay method of above (1), wherein the contact is made by forming a label phase at a position halfway up to the immobilized phase, the label phase comprising the labeled immunity substance in such a manner that the labeled immunity substance can be released from the base material upon contact with water, allowing the test sample to be absorbed from one end of the water-absorbable base material, thereby to form a complex of said labeled immunity substance and the assay target substance, and binding said complex with the first immunity substance at the immobilized phase.

(6) An immunoassay device comprising an immobilized phase comprising plural first immunity substances each capable of specifically binding with an assay target substance immobilized on a water-absorbable base material, and a label phase comprising a labeled immunity substance comprising a second immunity substance that is labeled with colored particles and capable of binding with said assay target substance, in such a manner that the labeled immunity substance can be released from the base material upon contact with water, said immobilized phase comprising at least two first immunity substances capable of specifically binding with at least two kinds of assay target substances selected from the group consisting of verotoxin-producing *Escherichia coli*, verotoxin and human hemoglobin contained in a test sample, said first immunity substances being immobilized on different positions on the base material.

(7) An immunoassay kit comprising an immobilized phase comprising, on a water-absorbable base material, plural immobilized first immunity substances each capable of specifically binding with an assay target substance, and a liquid containing labeled immunity substances each comprising a second immunity substance that is labeled with colored particles and capable of binding with said assay target substance, said assay target substance being at least two kinds of assay target substances selected from the group consisting of verotoxin-producing *Escherichia coli*, verotoxin and human hemoglobin.

DETAILED DESCRIPTION OF THE INVENTION

Figure 1:
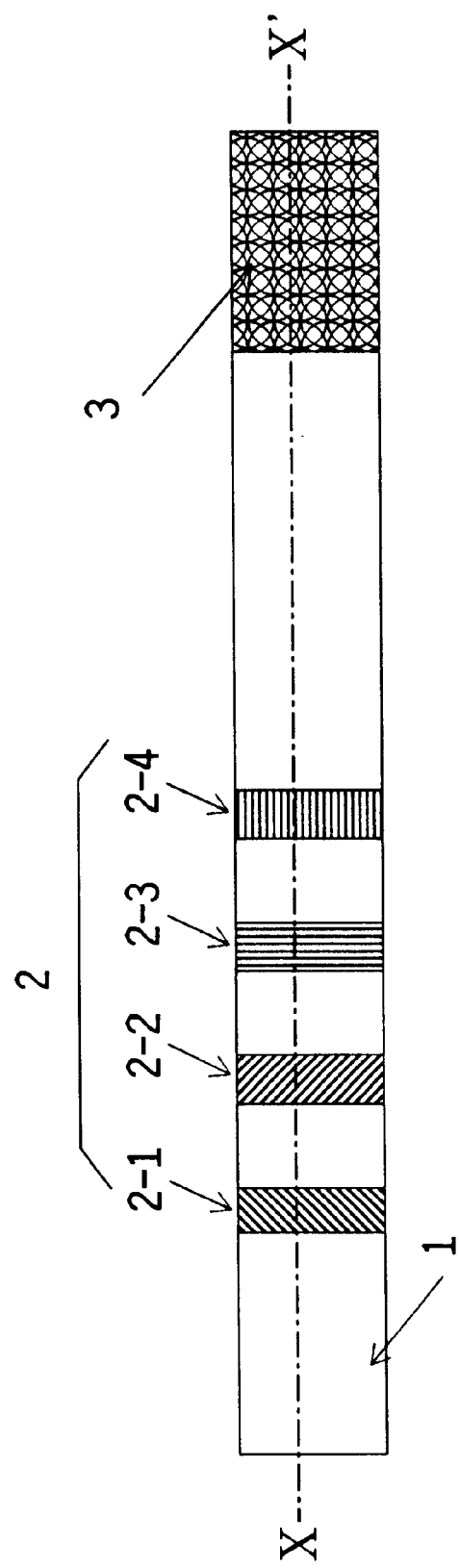
FIG. 1 is a plane view schematically showing one embodiment of the immunoassay strip of the present invention prepared in Example 1. In the Figure, 1 is a water-absorbable base material, 2 is an immobilized phase and 3 is a polyester nonwoven fabric.
Figure 2:
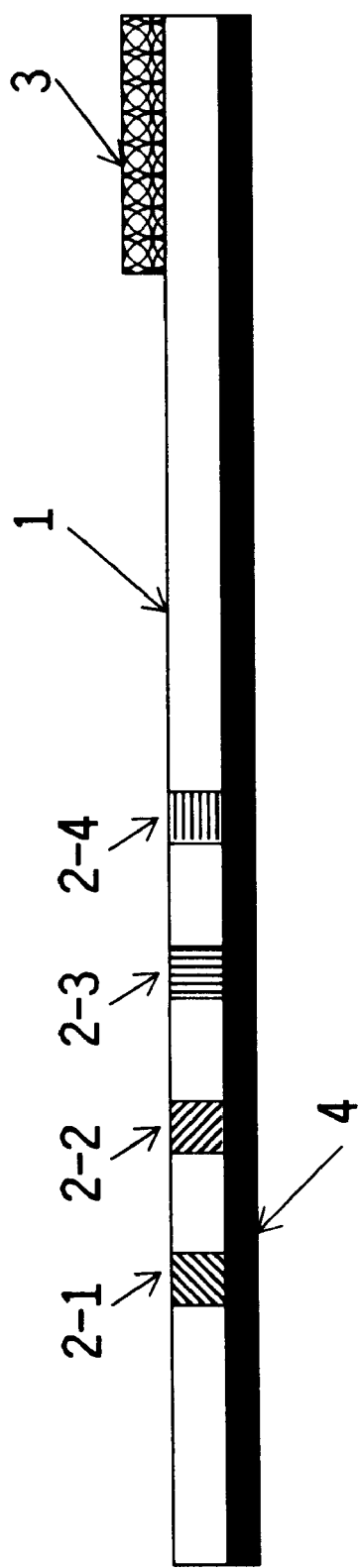
FIG. 2 is a cross sectional view along the line X–X' of the immunoassay strip of FIG. 1. In the Figure, 1 is a water-absorbable base material, 2 is an immobilized phase, 3 is a polyester nonwoven fabric and 4 is a polyester film.
Figure 3:
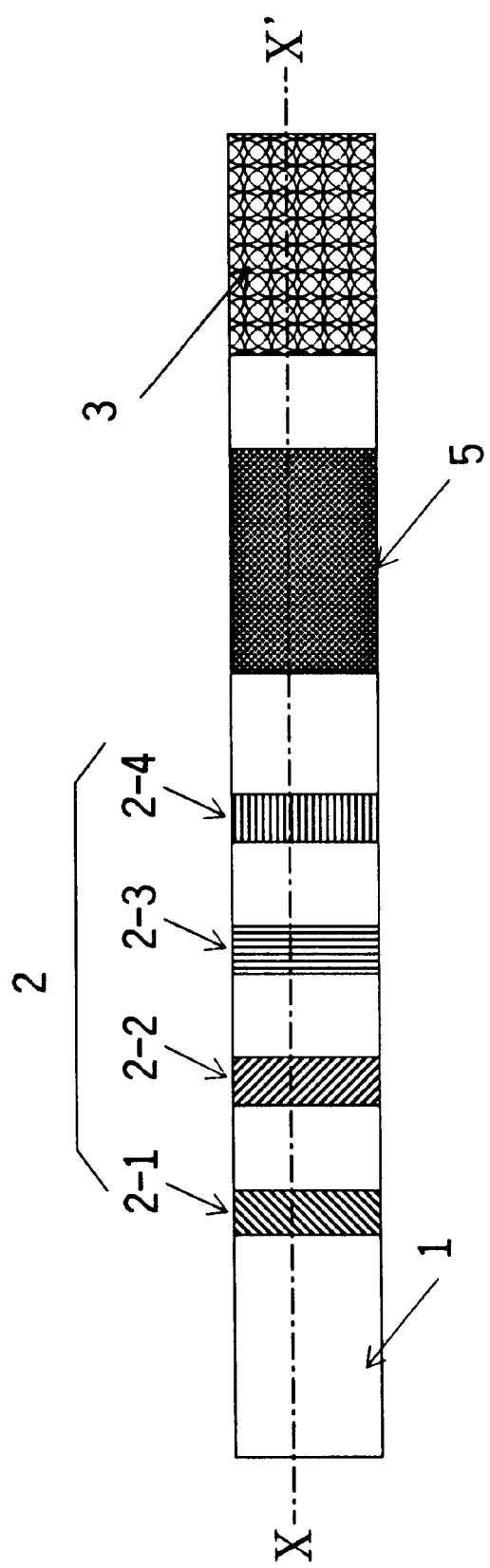
FIG. 3 is a plane view schematically showing one embodiment of the immunoassay strip of the present invention prepared in Example 4. In the Figure, 1 is a water-absorbable base material, 2 is an immobilized phase, 3 is a polyester nonwoven fabric and 5 is a label phase.
Figure 4:
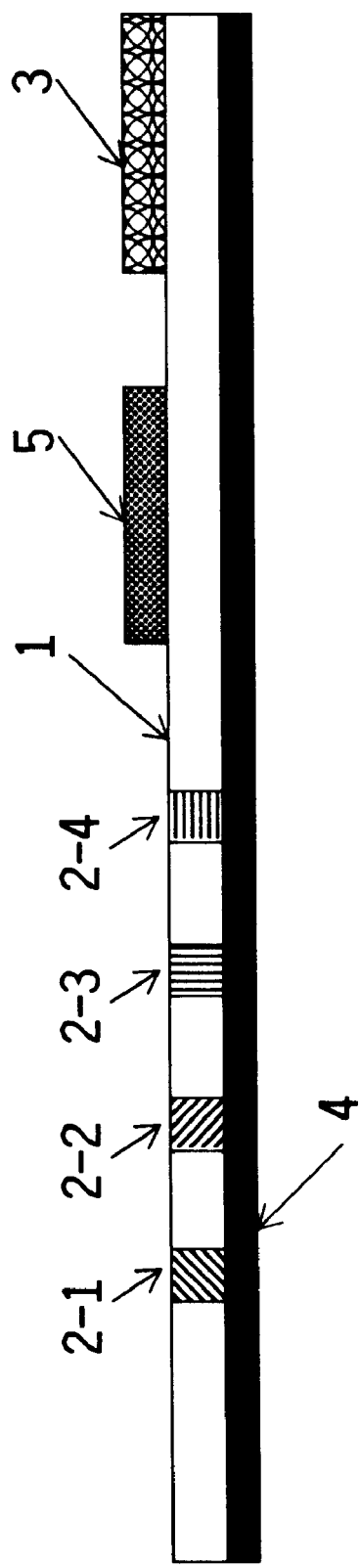
FIG. 4 is a cross sectional view along the line X–X' of the immunoassay strip of FIG. 3. In the Figure, 1 is a water-absorbable base material, 2 is an immobilized phase, 3 is a polyester nonwoven fabric, 4 is a polyester film, and 5 is a label phase.

In the present invention, the first immunity substance and the second immunity substance are antibodies that specifically bind with verotoxin-producing *Escherichia coli* (hereinafter to be referred to as VTEC), verotoxin (hereinafter to be referred to as VT) or human hemoglobin thereinafter to be referred to as Hb) as an assay target substance. The first immunity substance and the second immunity substance bind with the same assay target substance. According to the present invention wherein simultaneous assay of two or more assay target substances can be achieved, plural first immunity substances and the second immunity substances can be used. They specifically bind with at least two kinds of assay target substances from among the above-mentioned assay target substances. The immunity substance may be known and may be the one used in sandwich assay method depending on the assay target substance to be assayed. The first immunity substance to be immobilized to form an immobilized phase and the second immunity substance to be used as a labeled immunity substance may be the same, or two kinds of antibodies recognizing different epitopes may be used, though subject to variation depending on the kind of antibody to be used and assay targets. As the immunity substance, a monoclonal antibody and a polyclonal antibody can be used. When one of the immunity substances is a monoclonal antibody, the other immunity substance is one that recognizes different epitope from the epitope said monoclonal antibody recognizes.

In the present invention, moreover, VTEC to be detected may be of various serum groups, which are exemplified by VTECs of serum groups of O157, O26, O111, O18, O114, O115, O128, O145 and the like. Inclusive of H antigen in the protein moiety of flagella, they are designated O157:H7, O157:H-, O26:H11, O26:H-, O111:H-, O18:H-, O114:H-, O115:H19, O128:H2, O145:H- and the like. Of these, the serum groups of VTEC that are effectively used in the present invention are O157, O26 and O111, which are specifically O157:H7, O157:H-, O26:H111, O26:H-, O111:H- and the like. VT in case of human includes VT-1 and VT-2 having different physicochemical properties and immunological properties. In the present invention, these two kinds of verotoxins can be detected simultaneously.

The water-absorbable base material to be used in the present invention, is capable of absorbing a test sample containing an assay target substance, such as a solution extracted from foodstuff and culture supernatant, feces suspension (dissolved) and the like. Alternatively, a base material capable of absorbing diluted solutions of the above-mentioned with a buffer, a liquid containing a labeled immunity substance and the like can be used. These are free of limitation as long as they are capable of absorbing the above-mentioned test samples. In the present invention, a water-absorbable base material is used to secure time for sufficient reaction between the assay target substance in a test sample and the labeled immunity substance or first immunity substance on the immobilized phase. When the water-absorbable base material shows inferior water absorption, the time necessary for an assay target substance to reach an immobilized phase, or when a label phase is set, to reach said label phase, becomes longer and a quick assay is not attainable.

On the other hand, when the water-absorbable base material shows too high a water absorption, the time necessary for sufficient reaction of an assay target substance in a test sample with a labeled immunity substance or a first immunity substance on the immobilized phase cannot be secured, thus making an accurate assay unattainable. Preferable examples of the base material include nonwoven fabric, filter paper, glass fiber fabric, glass filter, nitrocellulose filter, porous material and the like. These base materials have suitable water absorption speed and allow easy, visual confirmation when colored particles bind to develop color.

In view of the above, the water absorption of the water-absorbable base material in the present invention is preferably demonstrated by about 0.5–5 cm of the length of the part of water absorption upon immersing one end of a 5 mm wide rectangular water-absorbable base material in water and leaving the strip for one minute.

For adjusting the water absorption of a base material, the surface of the base material may be covered with a hydrophilic polymer or surfactant, or immersed therein. Moreover, the water-absorbable base material may be made from a single material, or a continuous base material obtained by connecting heterogeneous materials with an optional adhesive means may be used.

In the present invention, the shape of the water-absorbable base material is not particularly limited as long as an assay target substance can be developed. For example, a rectangular sheet (strip) or a rod-shaped base material may be preferably used.

In the present invention, by the immobilized phase is meant the area where a first immunity substance capable of binding with an assay target substance is immobilized on a water-absorbable base material. The method for immobilizing the first immunity substance (preparation method of immobilized phase) on a water-absorbable base material is not particularly limited. A conventionally known physical method and a covalent bond method are suitable. In particular, the covalent bond method is preferable, wherein the immunity substance is hardly released from the base material. When the water-absorbable base material does not have a functional group for the above-mentioned covalent bond method, a base material is prepared using a polymer having a suitable functional group and attached to the water-absorbable base material to the extent the water absorption property is not impaired. Alternatively, a solution containing a first immunity substance and a hydrophilic polymer is applied to a water-absorbable base material and immersed into a coagulant solvent to coagulate the above-mentioned hydrophilic polymer, whereby an immobilized phase can be prepared. Examples of the hydrophilic polymer include hydroxypropylmethyl cellulose, poly(vinyl alcohol), hydroxyethyl cellulose and the like. Examples of the coagulant solvent include acetone, ethanol, methanol, ether and the like.

The amount of the first immunity substance to be immobilized varies depending on the kind and property of the immunity substance to be used. In general terms, an antibody to VTEC is applied in an amount of 0.001–0.5 mg/cm$^2$, an antibody to VT is applied in an amount of 0.01–1 mg/cm$^2$, an antibody to Hb is applied in an amount of 0.01–1 mg/cm$^2$.

The immobilized phase in the present invention comprises at least two first immunity substances immobilized on the water-absorbable base material at different positions. In order to trap the second immunity substances labeled with colored particles (labeled immunity substances) that migrated by liquid absorption to be mentioned later, at the immobilized phase, and to allow color development of each assay target substance, the first immunity substances are preferably immobilized on the water-absorbable base material at an interval of not less than 1 mm, preferably 5 mm, so that the developed colors will not mingle with the adjacent color.

The labeled immunity substance in the present invention comprises colored particles that label a second immunity substance capable of binding with an assay target substance. The colored particles may be any as long as they can be perceived visually. They are exemplified by colloidal particles of metals such as gold, silver, copper and the like, pigments represented by Sudan blue, Sudan red IV, Sudan III, Oilorange, Quinizarin green and the like, colored latex wherein latex has been colored with dye, and the like. From the aspect of visual observation, gold colloid and colored latex in blue and red, green or orange are preferably used, with particular preference given to colored latex made from water dispersible polymer particles colored in blue or red, in view of water dispersibility, dispersion stability and easy adjustment of detection sensitivity of assay target substance.

The size of the aforementioned colored particles is set to fall in the range of 0.01–3 $\mu$m, preferably 0.05–0.5 $\mu$m, in view of storage stability and easiness of preparation. When the particle size is too small, the degree of coloring per particle is also small, such that visual observation becomes difficult due to poor color development upon binding with the immobilized phase. When the size is too large, a slight agglomeration of colored particles may cause clogging in the water-absorbable base material, which in turn may result in degraded water absorption and non-specific color development.

The colored particles may be bound with the second immunity substance by a method conventionally known, such as a covalent bond method, physical adsorption method, ionic bond method and the like. In view of the absence of release of immunity substance after binding and superior stability, a covalent bond method is preferably employed. For the detection of plural assay target substances in a test sample, the corresponding plural immunity substances are bound with different kinds of colored particles in the present invention. The colored particles used for this purpose may have the same color or different color.

In the present invention, the labeled immunity substance is dispersed in a buffer etc. to give a liquid, which may be absorbed from one end of the water-absorbable base material having an immobilized phase. Alternatively, it may be contained in the water-absorbable base material, so that a labeled immunity substance can be released from the water-absorbable base material upon contact with water, when the labeled immunity substance contacts with the test sample. In the present invention, the label phase refers to an area where the labeled immunity substance is comprised in such a manner that enables release thereof from the base material upon contact with water.

The buffer in which the labeled immunity substance is dispersed has a pH and salt concentration that do not inhibit antigen-antibody reaction. The labeled immunity substance concentration during detection is 0.005–5%, preferably 0.01–0.5%. When the concentration is too low, the particles bound with the immobilized phase decreases in number, thus resulting in poor color development. When it is too high, not only an economic problem but also an obscure color development of the immobilized phase occur, that is caused by excess colored particles remaining in the area other than the immobilized phase. Hereinafter the liquid containing a labeled immunity substance is also referred to as a labeled immunity substance liquid.

The labeled immunity substance is contained in the water-absorbable base material (preparation of a label phase) by, for example, applying a solution containing a labeled immunity substance to a water-absorbable base material and drying same under suitable conditions. The solution may be dried by lyophilization. A different method includes dispersing a labeled immunity substance in a water soluble polymer or a saccharose solution, applying this dispersion liquid to a water-absorbable base material and drying. This method is advantageous for the preparation of the immunoassay strip of the present invention. When brought into contact with a test sample, a water soluble polymer or saccharose is easily solubilized in water and the labeled immunity substance is quickly released from the base material and reacts with the assay target substance. By adjusting the concentration of the water soluble polymer or saccharose, a solution having a suitable viscosity can be obtained, so that a labeled immunity substance can be contained in a specific area of the water-absorbable base material and the labeled immunity substance is free of coagulation or deformation upon drying. After drying, moreover, the labeled immunity substance is hardly released from the water-absorbable base material.

Examples of the water soluble polymer to be used in the above-mentioned way include poly(vinylpyrrolidone), poly (vinyl alcohol), poly(ethylene glycol), cellulose ether (e.g., methyl cellulose, ethyl cellulose, carboxymethyl cellulose, carboxyethyl cellulose, oxyethyl cellulose, cyan ethyl cellulose and the like), gelatin and the like.

In the present invention, the distance between the above-mentioned immobilized phase and the part where absorption of the test sample and/or the liquid containing labeled immunity substance is initiated (hereinafter to be referred to as liquid absorption part), or when an immunoassay strip having a label phase is used, the distance between the immobilized phase and the label phase, is 1–6 cm, preferably about 3–4 cm. When the distance is too great, the assay target substance may not reach the immobilized phase, or color development becomes too intense, or assay takes too long. Conversely, when the distance is too short, the color development at the immobilized phase becomes inconsistent or too low.

The amount of the labeled immunity substance to be applied in the label phase is free of particular limitation as long as it is sufficient to achieve the concentration of the labeled immunity substance during the detection. The amount is about 0.005–5 mg/cm$^2$ in the weight of a latex solid.

The liquid absorption part is not particularly limited as long as it does not prevent transfer of the test sample or a liquid containing a labeled immunity substance toward the water-absorbable base material. It may be the same base material, or a laminate of nonwoven fabric or woven fabric attached to said water absorbable base material.

In the present invention, moreover, an immobilized phase where the first immunity substance is immobilized, and a water-absorbable base material having a liquid absorption part is also referred to as an immunoassay device of the present invention. The shape of the immunoassay device of the present invention is free of limitation and may be, for example, a sheet, strip or rod. This immunoassay device may contain an immobilized phase, a liquid absorption part and a label phase.

The inventive immunoassay method includes the following methods. In a first method, a test sample to be subjected to an assay and a labeled immunity substance liquid are mixed. At this time, plural assay target substances (VTEC, VT, Hb) in the test sample are each bound with the labeled immunity substance to respectively form a labeled immunity substance—assay target substance complex [labeled immunity substance (colored particle—second immunity substance)—assay target substance]. Then, a mixture of the test sample and the labeled immunity substance liquid is absorbed from one end of the water-absorbable base material having an immobilized phase. The complex formed in the mixture moves through the water-absorbable base material along with the movement of the liquid to reach the immobilized phase. At the immobilized phase, the complex is bound with the first immunity substance immobilized on the immobilized phase to newly form a labeled immunocomplex comprising [labeled immunity substance (colored particle—second immunity substance)—assay target substance—first immunity substance], whereby the complex is immobilized and bound on the immobilized phase.

In a second method, a test sample alone is absorbed from one end of the water-absorbable base material having an immobilized phase. Each assay target substance in the test sample is bound with the first immunity substance on the immobilized phase (assay target substance—first immunity substance). According to this method, the test sample is liquid, and when solid, it is dissolved in a suitable buffer etc. and subjected to a treatment such as suspending, so that it can be absorbed by the water-absorbable base material. Then, the labeled immunity substance liquid is absorbed, whereby each labeled immunity substance forms a complex with the assay target substance bound with the immobilized phase to give a labeled immunocomplex comprising [labeled immunity substance (colored particle—second immunity substance)—assay target substance—first immunity substance], whereby the complex is immobilized and bound on the immobilized phase.

According to a third method, a labeled immunity substance liquid is absorbed from one end of the water-absorbable base material having an immobilized phase. A liquid or solid test sample is absorbed or applied at halfway up to the immobilized phase. The plural assay target substances in the test sample respectively form a complex with the labeled immunity substance. Thus formed complex moves through the water-absorbable base material along with the movement of the liquid to reach the immobilized phase. At the immobilized phase, the complex binds with the first immunity substance bound with the immobilized phase to newly form a labeled immunocomplex comprising [labeled immunity substance (colored particle—second immunity substance)—assay target substance—first immunity substance], whereby the complex is immobilized and bound on the immobilized phase.

When the inventive immunoassay strip on which a label phase has been previously formed is to be used, the following method is employed. First, a test sample to be subjected to an assay is absorbed from one end of the water-absorbable base material having an immobilized phase. In this method, also, the test sample is liquid, and when solid, it is dissolved in a suitable buffer etc. and subjected to a treatment such as suspending, so that it can be absorbed by the water-absorbable base material. The test sample moves through the water-absorbable base material to reach the label phase and liberates the labeled immunity substance from the base material. The plural assay target substances (VTEC, VT, Hb) contained in the test sample bind with respective labeled immunity substances to each form a complex of the labeled immunity substance and the assay target substance [labeled immunity substance (colored particle—second immunity substance)—assay target substance]. Then, the thus formed complex moves through the water-absorbable base material along with the movement of the liquid to reach the immobilized phase. At the immobilized phase, the complex binds with the first immunity substance bound with the immobilized phase to newly form a labeled immunocomplex comprising [labeled immunity substance (colored particle—second immunity substance)—assay target substance—first immunity substance], whereby the complex is immobilized and bound on the immobilized phase.

The colored particles constituting the labeled immunity substance gather at one part due to immobilization, where they collectively produce clear color development that enables visual confirmation of the existence of the assay target substance. Inasmuch as the immobilized phase comprises first immunity substances corresponding to plural assay target substances at different positions in the present invention, at least two kinds of assay target substances from VTEC, VT and Hb can be detected for their presence.

Therefore, the present invention enables simultaneous detection of VTEC and VT present in food or Hb co-existent with VTEC and/or VT present in feces.

The immunoassay method of the present invention is advantageously embodied by the inventive immunoassay kit or immunoassay device. The water-absorbable base material comprising an immobilized phase on which a first immunity substance capable of binding with an assay target substance has been immobilized, and a liquid containing a labeled immunity substance bound with a second immunity substance that is labeled with colored particles and capable of binding with said assay target substance, or a label phase comprising said labeled immunity substance, that constitute the kit, are the same as those mentioned above.

When an assay is done using the inventive immunoassay method, immunoassay device or assay kit, a test sample in a liquid of 1–500 $\mu$l, an assay target substance of VTEC of $10^2$–$10^9$ cfu, VT of 0.01–100,000 ng and Hb of 0.5–500,000 ng, can be preferably assayed, though subject to change depending on the kind and size of water-absorbable base material to be used and properties of immunity substance to be used.

The present invention is described in more detail by way of examples, to which the present invention is not limited.

Example 1
Detection of assay target substance (1)
1) Preparation of labeled immunity substance liquid To a dispersion (3 ml) containing blue-colored carboxylated polystyrene latex particles (solid concentration 5 wt % average particle size 0.1 $\mu$m, 0.01M-borate buffer, pH 8) were added water soluble carbodiimide (1 ml, 1 mg/ml, 0.01M-borate buffer, pH 8) and anti-*Escherichia coli* O157:H7 antibody (1 ml, goat IgG (manufactured by Kirkegaard & Perry Laboratories Inc.), 1 mg/ml, 0.01M-borate buffer, pH 8), and the mixture was reacted at 10° C. for 3 hr. The reaction mixture was washed by centrifugation using 0.01 M borate buffer (pH 8) as a washing solution to give blue-colored latex particle-labeled anti-*Escherichia coli* O157:H7 antibody (solid concentration 2 wt %).

In the same manner as above, anti-Verotoxin 1 antibody (mouse IgG, 1 mg/ml) and anti-verotoxin 2 antibody (mouse IgG, 1 mg/ml) were independently bound with a separate dispersion of green-colored carboxylated polystyrene latex particles (average particle size 0.1 $\mu$m).

In the same manner as above, anti-human hemoglobin antibody (rabbit IgG (manufactured by Nippon Bio-Test Laboratories Inc.), 5 mg/ml) was bound with red-colored carboxylated polystyrene latex particles (average particle size 0.1 $\mu$m).

Then, each latex particle-labeled antibody was suspended in 0.01 M-borate buffer (pH 8, each solid concentration 2 wt %).

2) Preparation of immobilized phase

On a nitrocellulose membrane (pore size 8 $\mu$m, 6 mm×60 mm, corresponding to 1 in Figures), at 30 mm from one end (2-4 in Figures), anti-*Escherichia coli* O157:H7 antibody (goat IgG, 1 mg/ml, 0.1 M phosphate buffer, pH 7.4) was applied, at 25 mm (2-3 in Figures), anti-verotoxin 1 antibody (rabbit IgG, 2 mg/ml) was applied, at 20 mm (2-2 in Figures), anti-verotoxin 2 antibody (rabbit IgG, 2 mg/ml) was applied, and at 15 mm (2-1 in Figures), anti-human hemoglobin antibody (rabbit IgG, 1 mg/ml) was applied in an amount of 1.5 $\mu$l each for draw a line with a dispenser.

This membrane was immersed in an aqueous solution of bovine serum albumin (1 wt %) and polyoxyethylene (10) octylphenylether (Wako Pure Chemical, 0.1 wt %) for 10 minutes and dried at 40° C. for 2 hr.

Then, a polyester film (90 $\mu$m thick, corresponding to 4 in Figures) was adhered to the back side of this membrane (opposite side from the surface on which antibody was applied) with a spray glue.

At 0–8 mm from the opposite end from the application of antibody, a polyester nonwoven fabric (6 mm×8 mm, thickness 2.5 mm, corresponding to 3 in Figures) was adhered to give the inventive immunoassay strip.

3) Assay

A test sample was prepared, which comprised 0.1 M phosphate buffer (containing NaCl (0.9 wt %), pH 7.4) and *Escherichia coli* O157:H7, verotoxin type 1, verotoxin type 2 and human hemoglobin dispersed therein at concentrations shown in Tables 1–3.

This test sample was mixed with the suspensions of colored latex labeled antibody (labeled immunity substance) prepared in 1) above to a solid concentration of 0.02 wt % each. After mixing and stirring, the mixed solution (60 $\mu$l) was dropwise added to the test strip of polyester nonwoven fabric prepared in 2) above, and the presence or absence of color development in 20 minutes was visually observed.

Tables 1–3 show the assay results when each assay target substance was used alone or in combination in the test sample. *Escherichia coli* O157:H7 used did not produce verotoxin, so that assay results of a mixed test sample would not be influenced. In each Table, the evaluation criteria were as follows.

+:line-like color development found on immobilized phase
−:line-like color development not found on immobilized phase

TABLE 1

| Test sample | | | | | | | |
|---|---|---|---|---|---|---|---|
| O157:H7 (cfu/ml) | $10^5$ | $10^5$ | $10^5$ | $10^5$ | 0 | $10^5$ |
| Verotoxin 1 (ng/ml) | 5 | 5 | 5 | 0 | 5 | 5 |
| Verotoxin 2 (ng/ml) | 5 | 5 | 0 | 5 | 5 | 0 |
| Human hemoglobin (ng/ml) | 100 | 0 | 100 | 100 | 100 | 0 |

TABLE 1-continued

| | | | | | | | |
|---|---|---|---|---|---|---|---|
| Immobilized phase | Anti- O157:H 7 antibody | + | + | + | + | − | + |
| | Anti-Verotoxin 1 antibody | + | + | + | − | + | + |
| | Anti-Verotoxin 2 antibody | + | + | − | + | + | − |
| | Anti-Human hemoglobin antibody | + | − | + | + | + | − |

TABLE 2

| | | | | | | |
|---|---|---|---|---|---|---|
| Test sample | O157:H7 (cfu/ml) | $10^5$ | $10^5$ | 0 | 0 | 0 |
| | Verotoxin 1 (ng/ml) | 0 | 0 | 5 | 5 | 0 |
| | Verotoxin 2 (ng/ml) | 5 | 0 | 5 | 0 | 5 |

TABLE 2-continued

| | | | | | | |
|---|---|---|---|---|---|---|
| | Human hemoglobin (ng/ml) | 0 | 100 | 0 | 100 | 100 |
| Immobilized phase | Anti-O157:H7 antibody | + | + | − | − | − |
| | Anti-Verotoxin 1 antibody | − | − | + | + | − |
| | Anti-Verotoxin 2 antibody | + | − | + | − | + |
| | Anti-Human hemoglobin antibody | − | + | − | + | + |

TABLE 3

| | | | | | | |
|---|---|---|---|---|---|---|
| Test sample | O157:H7 (cfu/ml) | $10^5$ | 0 | 0 | 0 | 0 |
| | Verotoxin 1 (ng/ml) | 0 | 5 | 0 | 0 | 0 |
| | Verotoxin 2 (ng/ml) | 0 | 0 | 5 | 0 | 0 |
| | Human hemoglobin ng/ml | 0 | 0 | 0 | 100 | 0 |
| Immobilized phase | Anti-O157:H7 antibody | + | − | − | − | − |
| | Anti-Verotoxin 1 antibody | − | + | − | − | − |
| | Anti-Verotoxin 2 antibody | − | − | + | − | − |
| | Anti-Human hemoglobin antibody | − | − | − | + | − |

Example 2
Detection of assay target substance (2)

In the same manner as in Example 1, the test samples (60 μl) prepared to have the concentrations shown in Tables 4–6 were dropwise added to the polyester nonwoven fabric part of the test strip prepared in Example 1, 2), and developed to the immobilized phase. Then, 0.1 M phosphate buffer (containing NaCl (0.9 wt %), pH 7.4) was added to dilute the solid component of each labeled immunity substance to a concentration of 0.02 wt %. The obtained labeled immunity substance liquid (60 μl) was dropwise added to the polyester nonwoven fabric part of the above-mentioned test strips and the presence or absence of the color development at the immobilized phase was visually observed 20 minutes later.

Tables 4–6 show the assay results when each assay target substance was used alone or in combination in the test sample.

TABLE 4

| | | | | | | | |
|---|---|---|---|---|---|---|---|
| Test sample | O157:H7 (cfu/ml) | $10^5$ | $10^5$ | $10^5$ | $10^5$ | 0 | $10^5$ |
| | Verotoxin 1 (ng/ml) | 5 | 5 | 5 | 0 | 5 | 5 |
| | Verotoxin 2 (ng/ml) | 5 | 5 | 0 | 5 | 5 | 0 |
| | Human hemoglobin (ng/ml) | 100 | 0 | 100 | 100 | 100 | 0 |
| Immobilized phase | Anti- O157:H 7 antibody | + | + | + | + | − | + |
| | Anti-Verotoxin 1 antibody | + | + | + | − | + | + |
| | Anti-Verotoxin 2 antibody | + | + | − | + | + | − |
| | Anti-Human hemoglobin antibody | + | − | + | + | + | − |

TABLE 5

| | | | | | | |
|---|---|---|---|---|---|---|
| Test sample | O157:H7 (cfu/ml) | $10^5$ | $10^5$ | 0 | 0 | 0 |
| | Verotoxin 1 (ng/ml) | 0 | 0 | 5 | 5 | 0 |
| | Verotoxin 2 (ng/ml) | 5 | 0 | 5 | 0 | 5 |
| | Human hemoglobin (ng/ml) | 0 | 100 | 0 | 100 | 100 |
| Immobilized phase | Anti-O157:H7 antibody | + | + | − | − | − |
| | Anti-Verotoxin 1 antibody | − | − | + | + | − |
| | Anti-Verotoxin 2 antibody | + | − | + | − | + |
| | Anti-Human hemoglobin antibody | − | + | − | + | + |

TABLE 6

| | | | | | | |
|---|---|---|---|---|---|---|
| Test sample | O157:H7 (cfu/ml) | $10^5$ | 0 | 0 | 0 | 0 |
| | Verotoxin 1 (ng/ml) | 0 | 5 | 0 | 0 | 0 |
| | Verotoxin 2 (ng/ml) | 0 | 0 | 5 | 0 | 0 |
| | Human hemoglobin (ng/ml) | 0 | 0 | 0 | 100 | 0 |
| Immobilized phase | Anti-O157:H7 antibody | + | − | − | − | − |
| | Anti-Verotoxin 1 antibody | − | + | − | − | − |
| | Anti-Verotoxin 2 antibody | − | − | + | − | − |
| | Anti-Human hemoglobin antibody | − | − | − | + | − |

Example 3
Detection of assay target substance (3)

In the same manner as in Example 1, the test samples (2 μl) prepared to have the concentrations shown in Tables 7–9 were absorbed in the surface side of the immunoassay strip prepared in Example 1, 2) at 12–20 mm from the opposite end from the part where the antibody was applied (immobilized phase). Then, 0.1 M phosphate buffer (containing NaCl (0.9 wt %), pH 7.4) was added to dilute the solid component of each labeled immunity substance to a concentration of 0.02 wt %. The labeled immunity substance liquid (60 μl) obtained upon mixture was dropwise added to the polyester nonwoven fabric part of the above-mentioned test strips and the presence or absence of the color development at the immobilized phase was visually observed 20 minutes later.

Tables 7–9 show the assay results when each assay target substance was used alone or in combination in the test sample.

TABLE 7

| | | | | | | | |
|---|---|---|---|---|---|---|---|
| Test sample | O157:H7 (cfu/ml) | $10^6$ | $10^6$ | $10^6$ | $10^6$ | 0 | $10^6$ |
| | Verotoxin 1 (ng/ml) | 150 | 150 | 150 | 0 | 150 | 150 |
| | Verotoxin 2 (ng/ml) | 150 | 150 | 0 | 150 | 150 | 0 |
| | Human hemoglobin (ng/ml) | 3 | 0 | 3 | 3 | 3 | 0 |
| Immobilized phase | Anti- O157:H 7 antibody | + | + | + | + | − | + |
| | Anti-Verotoxin 1 antibody | + | + | + | − | + | + |
| | Anti-Verotoxin 2 antibody | + | + | − | + | + | − |
| | Anti-Human hemoglobin antibody | + | − | + | + | + | − |

TABLE 8

| | | | | | | |
|---|---|---|---|---|---|---|
| Test sample | O157:H7 (cfu/ml) | $10^6$ | $10^6$ | 0 | 0 | 0 |
| | Verotoxin 1 (ng/ml) | 0 | 0 | 150 | 150 | 0 |
| | Verotoxin 2 (ng/ml) | 150 | 0 | 150 | 0 | 150 |
| | Human hemoglobin ng/ml | 0 | 3 | 0 | 3 | 3 |
| Immobilized phase | Anti-O157:H7 antibody | + | + | − | − | − |
| | Anti-Verotoxin 1 antibody | − | − | + | + | − |
| | Anti-Verotoxin 2 antibody | + | − | + | − | + |
| | Anti-Human hemoglobin antibody | − | + | − | + | + |

TABLE 9

| | | | | | | |
|---|---|---|---|---|---|---|
| Test sample | O157:H7 (cfu/ml) | $10^6$ | 0 | 0 | 0 | 0 |
| | Verotoxin 1 (ng/ml) | 0 | 150 | 0 | 0 | 0 |
| | Verotoxin 2 (ng/ml) | 0 | 0 | 150 | 0 | 0 |
| | Human hemoglobin (ng/ml) | 0 | 0 | 0 | 3 | 0 |
| Immobilized phase | Anti-O157:H7 antibody | + | − | − | − | − |
| | Anti-Verotoxin 1 antibody | − | + | − | − | − |
| | Anti-Verotoxin 2 antibody | − | − | + | − | − |
| | Anti-Human hemoglobin antibody | − | − | − | + | − |

Example 4
Detection of assay target substance (4)
1) Preparation of immunoassay strip The blue-colored latex particle-labeled anti-*Escherichia coli* O157:H7 antibody dispersion (1 ml, solid concentration 2 wt %) prepared in Example 1, 1), green-colored latex particle-labeled anti-verotoxin 1 antibody dispersion (1 ml, solid concentration 2 wt %), green-colored latex particle-labeled anti-verotoxin 2 antibody dispersion (1 ml, solid concentration 2 wt %), red-colored latex particle-labeled anti-human hemoglobin antibody dispersion (1 ml, solid concentration 2 wt %) and aqueous solution of saccharose (6 ml, 20 wt %) were mixed and a rayon nonwoven fabric (6 mm×8 mm) was impregnated with this mixture (10 μl) and dried at 40° C. for 2 hr.

This nonwoven fabric containing colored latex particle-labeled antibodies was adhered to the front surface of the membrane having an immobilized phase prepared in Example 1, 2) wherein a polyester film (90 μm thick) was adhered to the back (the opposite side from the antibody application side) as in Example 1, at 12–20 mm from the opposite end from the immobilized phase. In addition, polyester nonwoven fabric (6 mm×8 mm, thickness 2.5 mm, corresponding to 3 in Figures) was adhered at 0–8 mm to give the immunoassay strip of the present invention.

2) Assay

*Escherichia coli* O157:H7, verotoxin type 1, verotoxin type 2 and human hemoglobin were dispersed in 0.1 M phosphate buffer (containing NaCl (0.9 wt %), pH 7.4) to the concentrations shown in Tables 10–14 to give test samples.

The obtained test sample (60 μl) was dropwise added to the polyester nonwoven fabric part of the above-mentioned test strips and the presence or absence of the color development at the immobilized phase was visually observed 20 minutes later.

Tables 10–13 show the assay results when each assay target substance was used alone or in combination in the test sample. Table 14 shows the assay results when each test sample was mixed and subjected to the assay. *Escherichia coli* O157:H7 used did not produce verotoxin, so that assay results of a mixed test sample would not be influenced. In each Table, the evaluation criteria were as in Example 1.

TABLE 10

Test sample of *E. coli* O157:H7 alone

| Immobilized phase | *E. coli* O157:H7 concentration (cells, cfu/ml) | | | | |
|---|---|---|---|---|---|
| | $10^3$ | $10^4$ | $10^5$ | $10^6$ | $10^7$ |
| Anti-*E. coli* O157:H7 antibody immobilized phase | − | − | + | + | + |
| Anti-verotoxin 1 antibody immobilized phase | − | − | − | − | − |
| Anti-verotoxin 2 antibody immobilized phase | − | − | − | − | − |
| Anti-human hemoglobin antibody immobilized phase | − | − | − | − | − |

TABLE 11

Test sample of Verotoxin 1 alone

| Immobilized phase | Verotoxin 1 concentration (ng/ml) | | | | |
|---|---|---|---|---|---|
| | 0.5 | 1.0 | 5.0 | 10 | 50 |
| Anti-*E. Coli* O157:H7 antibody immobilized phase | − | − | − | − | − |
| Anti-verotoxin 1 antibody immobilized phase | − | + | + | + | + |

TABLE 11-continued

Test sample of Verotoxin 1 alone

| Immobilized phase | Verotoxin 1 concentration (ng/ml) | | | | |
|---|---|---|---|---|---|
| | 0.5 | 1.0 | 5.0 | 10 | 50 |
| Anti-verotoxin 2 antibody immobilized phase | − | − | − | − | − |
| Anti-human hemoglobin antibody immobilized phase | − | − | − | − | − |

TABLE 12

Test sample of Verotoxin 2 alone

| Immobilized phase | Verotoxin 2 concentration (ng/ml) | | | | |
|---|---|---|---|---|---|
| | 0.5 | 1.0 | 5.0 | 10 | 50 |
| Anti-*E. Coli* O157:H7 antibody immobilized phase | − | − | − | − | − |
| Anti-verotoxin 1 antibody immobilized phase | − | − | − | − | − |
| Anti-verotoxin 2 antibody immobilized phase | − | − | + | + | + |
| Anti-human hemoglobin antibody immobilized phase | − | − | − | − | − |

TABLE 13

Test sample of human hemoglobin alone

| Immobilized phase | human hemoglobin concentration (ng/ml) | | | | |
|---|---|---|---|---|---|
| | 10 | 50 | 100 | 500 | 1000 |
| Anti-*E. coli* O157:H7 antibody immobilized phase | − | − | − | − | − |
| Anti-verotoxin 1 antibody immobilized phase | − | − | − | − | − |
| Anti-verotoxin 2 antibody immobilized phase | − | − | − | − | − |
| Anti-human hemoglobin antibody immobilized phase | − | + | + | + | + |

TABLE 14

Test sample mixture of assay target substance

| | | | | | | | |
|---|---|---|---|---|---|---|---|
| Test sample | O157:H7 (cfu/ml) | $10^5$ | $10^5$ | $10^5$ | $10^5$ | $10^5$ | 0 |
| | Verotoxin 1 (ng/ml) | 5 | 5 | 0 | 5 | 0 | 5 |
| | Verotoxin 2 (ng/ml) | 5 | 5 | 0 | 0 | 5 | 5 |
| | Human hemoglobin (ng/ml) | 100 | 0 | 100 | 100 | 100 | 100 |
| Immobilized phase | Anti- O157:H7 antibody | + | + | + | + | + | − |
| | Anti-Verotoxin 1 antibody | + | + | − | + | − | + |
| | Anti-Verotoxin 2 antibody | + | + | − | − | + | + |
| | Anti-Human hemoglobin antibody | + | − | + | + | + | + |

As is evident from the above results, the immunoassay method, the immunoassay device and the immunoassay kit of the present invention enable easy and simultaneous analysis of O157 (VIEC), VT and Hb in a test sample, and enable detection with precision at the same level as individual analysis. Inasmuch as the analysis depends on color development, visual observation gives qualitative or semi-qualitative analysis. Using an optical device, quantitative analysis becomes possible.

This application is based on application No. 213177/1997 filed in Japan, the content of which is incorporated hereinto by reference.

What is claimed is:

1. An immunoassay method for detecting bacterial infection by Verotoxin-producing *Escherichia coli*, in a test sample comprising:
   (a) bringing an immobilized phase comprising, at different positions on a water-absorbable base material, at least two first immunity substances that specifically bind to at least two different kinds of assay target substances wherein one of the assay target substances is human hemoglobin and the other assay target substances are selected from the group consisting of verotoxin-producing *Escherichia Coli* and verotoxin, into contact with
      (1) the test sample; and
      (2) a liquid containing second immunity substances, each of said second immunity substance is labeled with colored latex particles and binds with said assay target substances, thereby to form assay target substance-labeled immunity substance complexes and to bind said complexes with respective first immunity substances at the immobilized phase; and
   (b) detecting said labeled immunity substance complex on said water-absorbable base material and relating the presence of said complexes to the presence of said analytes in the test sample.

2. The immunoassay method of claim 1, wherein contact between the test sample and the second immunity substances is made by positioning a label phase partially up the immobilized phase by adding the liquid containing the second immunity substance partially up the immobilized phase and drying the liquid, the label phase comprising the second immunity substance in such a manner that the second immunity substance can be released from the base material upon contact with water, allowing the test sample to be absorbed from one end of the water-absorbable base material, thereby to form a complex of said second immunity substance and the assay target substance, and binding said complex with the first immunity substance at the immobilized phase.

3. The method of claim 1 wherein said immobilized phase includes at least three first immunity substances specific for at least three different kinds of assay target substances wherein the assay target substances are human hemoglobin, verotoxin-producing *Escherichia coli*, and verotoxin.

4. An immunoassay device for detecting bacterial infection by verotoxin-producing *E. coli* in a fecal test sample comprising:
   an immobilized phase comprising a plurality of first immunity substances that specifically bind to a plurality of assay target substances, wherein at least one of said first immunity substances specifically bind to human hemoglobin and the other of said first immunity substances specifically bind to assay target substances selected from the group consisting of verotoxin-producing *E. coli* and verotoxin; said first immunity substances are immobilized at different positions on a water-absorbable base material; and a label phase, on the water-absorbable base material, comprising second immunity substances, said second immunity substances are labeled with colored latex particles and bind with one of said assay target substances in such a manner that the second immunity substance can be released from the water-absorbable base material upon contact with water.

5. The device of claim 4 wherein said immobilized phase includes at least three first immunity substances specific for at least three different kinds of assay target substances wherein the assay target substances are human hemoglobin, verotoxin-producing *Escherichia coli*, and verotoxin.

6. An immunoassay kit comprising:

an immobilized phase comprising, a plurality of first immunity substances that specifically bind to a plurality of assay target substances, wherein at least one of said first immunity substances specifically bind to human hemoglobin and the other of said first immunity substances specifically bind to assay target substances selected from the group consisting of verotoxin-producing *E. coli* and verotoxin; said first immunity substances are immobilized at different positions on a water-absorbable base material; and a liquid containing second immunity substances, each of said second immunity substances is labeled with colored latex particles and is specific for at least one of said assay target substances, said assay target substances being at least two different kinds of assay target substances wherein one of the assay target substances is human hemoglobin and the other assay target substances are selected from the group consisting of verotoxin-producing *Escherichia coli* and verotoxin.

7. The kit of claim 6 wherein said immobilized phase includes at least three first immunity substances specific for at least three different kinds of assay target substances wherein the assay target substances are human hemoglobin, verotoxin-producing *Escherichia coli*, and verotoxin.

* * * * *